US00PP21978P3

(12) United States Plant Patent
Valstar

(10) Patent No.: US PP21,978 P3
(45) Date of Patent: Jun. 14, 2011

(54) *CALATHEA* PLANT NAMED 'HGV09'

(50) Latin Name: *Calathea rosea picta*
Varietal Denomination: HGV09

(76) Inventor: Oscar Valstar, Maasland (NL)

( * ) Notice: Subject to any disclaimer, the term of this patent is extended or adjusted under 35 U.S.C. 154(b) by 0 days.

(21) Appl. No.: 12/589,197

(22) Filed: Oct. 19, 2009

(65) Prior Publication Data

US 2011/0093994 P1 Apr. 21, 2011

(51) Int. Cl.
*A01H 5/00* (2006.01)

(52) U.S. Cl. ..... Plt./375
(58) Field of Classification Search ..... Plt./375
See application file for complete search history.

(56) References Cited

OTHER PUBLICATIONS

Upov Plant Variety Database 2010/05. p. 1.*

* cited by examiner

*Primary Examiner* — Annette H Para

(57) ABSTRACT

A new and distinct *Calathea rosea picta* cultivar named 'HGV09' is disclosed, characterized by unique coloration of the foliage. The new variety is a *Calathea*, and is normally used as an ornamental plant.

1 Drawing Sheet

Figure 1:
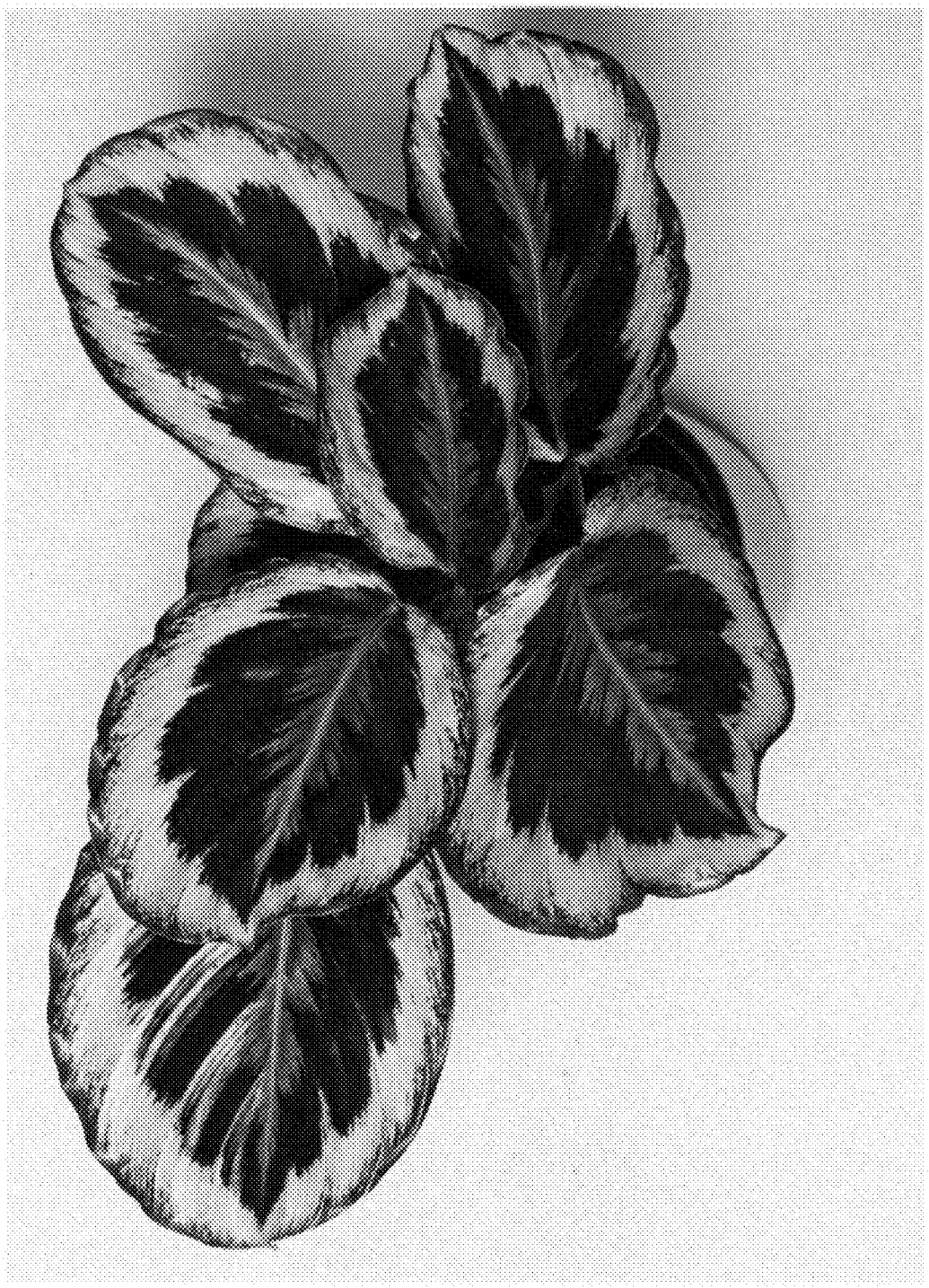

Latin name of the genus and species: *Calathea rosea picta.*
Variety denomination: 'HGV09'.

BACKGROUND OF THE INVENTION

The new cultivar was discovered as a chance, whole plant mutation in a commercial nursery in Maasland, the Netherlands. The inventor, Oscar Valstar, a citizen of the Netherlands, discovered the new variety as a naturally occurring whole plant mutation among several hundred plants of the unpatented commercial variety, *Calathea rosea picta* 'Medallion'. The new variety was discovered in October 2005 by the inventor.

Asexual reproduction of the new cultivar 'HGV09' by tissue culture was performed at a commercial nursery in Maasland, the Netherlands in November 2005. Since that time, many generations have been reproduced, and have shown that the unique features of this cultivar are stable and reproduced true to type through successive generations.

SUMMARY OF THE INVENTION

The cultivar 'HGV09' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'HGV09.' These characteristics in combination distinguish 'HGV09' as a new and distinct *Calathea rosea picta* cultivar:

1. Distinctive variegation pattern unlike other known *Calathea rosea picta* cultivars.
2. Unique purple underleaf coloration.

PARENT COMPARISON

Plants of the new cultivar 'HGV09' are similar to plants of the parent variety *Calathea rosea picta* 'Medallion' in most horticultural characteristics. However, plants of the new cultivar 'HGV09' produce different colored foliage

BRIEF DESCRIPTION OF THE PHOTOGRAPH

The accompanying photograph in FIG. 1 illustrates in full color a typical plant of 'HGV09' grown in a greenhouse. The pot size is a commercial 15 cm container. The plant shown is approximately 4.5 months old. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'HGV09' plants grown in a commercial greenhouse in Maasland, The Netherlands from Spring to Fall. The growing temperature ranged from approximately 20 to 21° C. at night and 20 to 22° C. during the day. Measurements and numerical values represent averages of typical flowering types. No chemical or photoperiodic treatments were given.
Botanical classification: *Calathea rosea picta* 'HGV09.'

PLANT

Growth habit: Outwardly spreading, fleshy, very tender perennial, suitable for indoor ornamental use.
Height: Approximately 22.6 cm.
Plant spread: Approximately 36 cm.
Growth rate: Moderate.
Branching characteristics: Approximately 3 main stems emerging directly from roots, no lateral branches.
Diameter of primary stem: Approximately 1.1 cm.
Length of primary stem: Approximately 4.2 cm.
Internode length: Average 0.2 cm.

Texture of stems: Smooth, moderately glossy.
Color of stems: Near RHS Greyed-Purple N186C.
Stem strength: Strong.
Number of leaves per stem: Average 4.
Age of plant described: Approximately 20 weeks.
Pot size of plant described: 13 cm.
Root description: Thick fleshy roots with fibrous secondary root system. Root color near RHs Grey-Brown 199C.

FOLIAGE

Leaf:

*Arrangement.*—Alternate, distichous.
*Average length.*—Approximately 14.4 cm.
*Average width.*—Approximately 11.8 cm.
*Shape of blade.*—Broad obovate.
*Aspect.*—Leaves horizontal to slightly drooping, average angle approximately 115° to stem, where horizontal is 0°.
*Apex.*—Abruptly acute.
*Base.*—Rounded.
*Attachment.*—Stalked.
*Margin.*—Entire, wavy.
*Texture of top surface.*—Smooth, glossy, leathery.
*Texture of bottom surface.*—Smooth, glossy, leathery.
*Color.*—Young foliage upper side: Darker than RHS Green 139A, blotched lighter, along main vein, near both Green 137B and 137C. Margins near both Greyed-Green 191A and 191B. Outermost edge of margin near N137C. Young foliage under side: Near RHS Greyed-Purple N186A, Margins near 187B. Mature foliage upper side: Near RHS Green 139A, but darker. Blotching along main vein near Green 137C. Margins near Greyed-Green 194B, with outermost edge near Green N137A. Irregular markings near Greyed-Purple 187D. Mature foliage under side: Near RHS Greyed-Purple N186A. Margins near 187A.

Venation:

*Type.*—Pinnate.
*Color.*—Upperside: Main vein near RHS Greyed-Purple 183B, secondary veins near Green 139A. Underside: Near RHS Greyed-Green 199A.

Petiole:

*Length.*—Average 10.5 cm.
*Width.*—Average 0.7 cm.
*Coloration.*—Near RHS Greyed-Purple 187A.

Petiole sheath:

*Length.*—Average 9.5 cm.
*Width.*—Average 0.8 cm.
*Coloration.*—Near RHS Greyed-Purple 187A.

FLOWER

Flowering not observed to date.

OTHER CHARACTERISTICS

Disease resistance: Neither resistance nor susceptibility to diseases or pests normal to *Calathea* has been observed in this variety.
Drought tolerance and temperature tolerance: Very tender perennial, low temperature damage occurs near 7° C. Tolerates high temperature to at least 40° C. No drought tolerance has been observed.
Fruit/seed production: Fruits and seeds have not been observed.

What is claimed is:

1. A new and distinct cultivar of *Calathea* plant named 'HGV09' as herein illustrated and described.

* * * * *